United States Patent
Takizawa et al.

(10) Patent No.: US 7,718,444 B2
(45) Date of Patent: May 18, 2010

(54) CONVENIENT DETECTION METHOD, DETECTION APPARATUS AND DETECTION KIT

(75) Inventors: Kazuyuki Takizawa, Niigata (JP); Ryo Shida, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 7 days.

(21) Appl. No.: 10/587,212

(22) PCT Filed: Jan. 27, 2005

(86) PCT No.: PCT/JP2005/001090

§ 371 (c)(1),
(2), (4) Date: May 21, 2007

(87) PCT Pub. No.: WO2005/071413

PCT Pub. Date: Aug. 4, 2005

(65) Prior Publication Data

US 2008/0193953 A1    Aug. 14, 2008

(30) Foreign Application Priority Data

Jan. 27, 2004    (JP) .............................. 2004-018886

(51) Int. Cl.
*G01N 33/53* (2006.01)

(52) U.S. Cl. ................ 436/518; 436/514; 436/535; 436/540; 436/541; 436/810; 436/818; 435/287.1; 435/287.7; 435/810; 435/970; 435/969; 422/56; 422/57; 422/58; 422/60; 422/61

(58) Field of Classification Search ................ 436/514, 436/518, 535, 540, 541, 810, 818; 435/287.1, 435/287.7, 810, 970, 969; 422/56–61
See application file for complete search history.

(56) References Cited

U.S. PATENT DOCUMENTS 4,806,311 A * 2/1989 Greenquist .................... 422/56

(Continued)

FOREIGN PATENT DOCUMENTS

JP    2001-33453    2/2001

(Continued)

OTHER PUBLICATIONS

Search Report EP 05704193.

*Primary Examiner*—Bao-Thuy L Nguyen
(74) *Attorney, Agent, or Firm*—Stephen A. Bent; Foley & Lardner LLP

(57) ABSTRACT

This invention provides a simple detection method with excellent sensitivity and specificity, which allows prompt detection of an analyte by allowing a labeled reagent to effectively react with the analyte in the process of treating an analyte-containing specimen, such as during removal of impurities, a detection apparatus, and a detection kit. This method for detecting an analyte in specimens comprises steps of: bringing a labeled reagent containing a ligand that specifically binds to the analyte into contact with a specimen; and supplying the mixture of the specimen and the labeled reagent to a solid-phase support onto which a capture reagent that specifically binds to the analyte has been immobilized, wherein the step of bringing the specimen into contact with the labeled reagent is carried out at a site that is not on the solid-phase support and that is detached from the solid-phase support. The invention also provides a detection apparatus comprising a solid-phase support onto which a capture reagent that specifically binds to the analyte in the specimen is immobilized and a kit for detecting an analyte in a specimen and a device for supplying a specimen comprising a labeled reagent containing a ligand that specifically binds to the analyte.

5 Claims, 12 Drawing Sheets

U.S. PATENT DOCUMENTS

| | | | |
|---|---|---|---|
| 4,916,056 A | * | 4/1990 | Brown et al. ................ 435/7.92 |
| 5,141,850 A | * | 8/1992 | Cole et al. .................. 436/525 |
| 2002/0173047 A1 | | 11/2002 | Hudak et al. |

FOREIGN PATENT DOCUMENTS

| | | |
|---|---|---|
| JP | 2003-511697 A | 3/2003 |
| WO | WO 01/27612 A2 | 4/2001 |
| WO | WO 02/08727 A1 | 1/2002 |
| WO | WO 03/016902 A1 | 2/2003 |
| WO | WO 03/098215 A1 | 11/2003 |
| WO | WO 2005/124347 A1 | 12/2005 |

* cited by examiner

CONVENIENT DETECTION METHOD, DETECTION APPARATUS AND DETECTION KIT

TECHNICAL FIELD

The present invention relates to a detection method for conducting qualitative or quantitative assay that specifically detects an analyte in a specimen, a detection apparatus, a detection kit, and a method for producing the same.

BACKGROUND ART

As methods of analysis for detecting or quantifying an analyte in a sample with the utilization of immune response specificity, a variety of methodologies, such as immunodiffusion, enzyme assay, and agglutination, have been put to practical use. In particular, detection methods by means of flow-through assay (detection) techniques ("Guide to Diagnostic Rapid Test Device Components," $2^{nd}$ edition, published by Scheicher & Schuell company, January 2000, Edited by Lisa Vickers, pp. 6-8 and JP Patent Publication (Kokoku) No. 7-34016B (1995)) or by means of immunochromatography assay (detection) techniques (a lateral-flow assay, a tangential-flow assay, JP Patent Publication (Kokoku) No. 7-13640B (1995), JP Patent No. 2890384) spread rapidly because of the convenience thereof in recent years. The principles of such detection methods are briefly described below. According to many of commercial flow-through assay techniques, a capture reagent (e.g., antibody) for capturing an analyte (e.g., antigens) is first immobilized on a membrane (a solid-phase support), and a given amount of a sample comprising an analyte-containing specimen suspended therein is supplied to the membrane. When the sample passes through the membrane, the existing analyte is captured by a capture reagent that has been immobilized on the membrane, and a complex of the analyte and the capture reagent is then formed. Subsequently, a given amount of a labeled reagent containing a ligand that specifically binds to the analyte (e.g., enzyme labels for the analyte) is supplied, and a complex of the capture reagent, the analyte, and the labeled reagent is formed at a site at which the capture reagent has been immobilized. The labeled reagent can be detected by any technique (in the case of an enzyme label, a color reaction takes place with the supply of a substrate) to determine the presence of the analyte.

Many types of commercial kits for immunochromatography assay techniques each comprise a strip membrane. The membrane comprises a capture reagent (e.g., antibody) for capturing an analyte (e.g., antigens) immobilized at one of its ends in the lengthwise direction, and a labeled reagent (e.g., colloidal gold particles that can be visualized) comprising a ligand that specifically binds to the analyte sustained in a spreadable manner on the membrane at the other end. If a given amount of a sample comprising an analyte-containing specimen suspended therein is supplied to the side of the membrane that sustains the labeled reagent, the analyte binds to the labeled reagent to form a complex of the analyte and the labeled reagent when the sample is spread over the membrane. The complex of the analyte and the labeled reagent spreads and flows over the membrane, and it is captured by the capture reagents immobilized on the membrane. Thus, a complex of the capture reagent, the analyte, and the labeled reagent is formed at a site at which the capture reagent has been immobilized. The presence of the analyte can be determined by detecting the labeled reagent by any technique (in the case of colloidal gold particles that can be visualized, an image of the aggregate thereof is to be detected).

In the many assay techniques, since large quantities of impurities were contained in analyte-containing specimens, a variety of types of chemical or physical preparations are carried out in order to remove the impurities. From such prepared samples, impurities are removed as much as possible, and the analyte is then extracted therefrom to form a complex of the capture reagent, the analyte, and the labeled reagent. This is an essential condition for an assay technique having high sensitivity and specificity. However, the procedures therefore are laborious and time consuming, which result in decreased operational efficiency. When an assay technique requires laboriousness, it often causes operational errors. This deteriorates the quality of the assay technique in terms of safety, costs, and operational efficiency.

Patent Document 1: JP Patent Publication (Kokoku) No. 7-34016B (1995)

Patent Document 2: JP Patent Publication (Kokoku) No. 7-13640B (1995)

Patent Document 3: JP Patent No. 2,890,384

Non-Patent Document 1: Guide to Diagnostic Rapid Test Device Components, $2^{nd}$ edition, published by Scheicher & Schuell company, January 2000, Edited by Lisa Vickers, pp. 6-8

DISCLOSURE OF THE INVENTION

The present invention provides a simple detection method with excellent sensitivity and specificity, which allows prompt detection of an analyte by allowing a labeled reagent to effectively react with the analyte in the process of preparing an analyte-containing specimen, such as during removal of impurities. The present invention also provides a detection apparatus and a detection kit.

The present inventors have conducted concentrated studies in order to develop a method that is capable of promptly and sensitively detecting an analyte, whereby impurities are effectively and assuredly removed from an analyte-containing specimen, furthermore, a complex of a capture reagent, an analyte, and a label agent is more effectively formed. As a result, they discovered that a complex of a capture reagent, an analyte, and a labeled reagent could be effectively formed without interference from impurities in the following manner. That is, an analyte is brought into contact with a labeled reagent containing a ligand that specifically binds to the analyte prior to supply thereof to a solid-phase support onto which a capture reagent has been immobilized. Impurities are removed via, for example, filtration using a filter, the analyte and the labeled reagent are then supplied to the solid-phase support onto which the capture reagent has been immobilized. This has led to the completion of the present invention.

A summary of the present invention is as follows.

[1] A method for detecting an analyte in a specimen comprising steps of: bringing a labeled reagent containing a ligand that specifically binds to the analyte into contact with a specimen; and supplying the mixture of the analyte and the labeled reagent to a solid-phase support onto which a capture reagent that specifically binds to the analyte has been immobilized, wherein the step of bringing the specimen into contact with the labeled reagent is carried out at a site detached from the solid-phase support.

[2] The method for detecting an analyte according to [1], wherein the step of bringing a labeled reagent containing a ligand that specifically binds to the analyte into contact with a specimen and the step of supplying the mixture of the analyte and the labeled reagent to a solid-phase support onto which a capture reagent that specifically binds to the analyte has been immobilized are carried out in a single step.

[3] The method for detecting an analyte according to [2], which further comprises a step of filtration for removing impurities, wherein the step of bringing a labeled reagent containing a ligand that specifically binds to the analyte into contact with a specimen, the step of filtration for removing impurities, and the step of supplying the mixture of the analyte and the labeled reagent to a solid-phase support onto which a capture reagent that specifically binds to the analyte has been immobilized are carried out in a single step.

[4] The method according to any of [1] to [3], which is carried out by a flow-through assay technique.

[5] The method according to any of [1] to [3], which is carried out by an immunochromatography assay technique.

[6] The method according to any of [1] to [5], wherein the step of bringing a labeled reagent containing a ligand that specifically binds to the analyte into contact with a specimen is carried out in a device for supplying a specimen containing a labeled reagent.

[7] The method according to [6], wherein the device for supplying an analyte comprises a means of filtration.

[8] The method according to [7], wherein the means of filtration comprises a labeled reagent.

[9] The method according to [1], which is carried out by a flow-through assay technique, wherein a porous material impregnated with a labeled reagent containing a ligand that specifically binds to the analyte is contained in an adaptor that can be provided in an upper layer of the solid-phase support onto which a capture reagent has been immobilized, a specimen is supplied to the adaptor to bring the specimen into contact with the labeled reagent containing a ligand that specifically binds to the analyte, and the mixture of the specimen and the labeled reagent is supplied to the solid-phase support onto which the capture reagent that specifically binds to the analyte has been immobilized.

[10] The method according to any of [1] to [9], wherein the labeled reagent is labeled with a substance selected from the group consisting of an insoluble particulate substance, an enzyme, a fluorescent dye, and a radioisotope.

[11] The method according to [10], wherein the labeled reagent is labeled with an enzyme, and the method comprises a step of supplying a substrate for the enzyme.

[12] The method according to any of [1] to [11], wherein the analyte is an antigen, and the ligand and the capture reagent are each an antibody that specifically binds to the antigen.

[13] The method according to any of [1] to [11], wherein the analyte is an antibody, and the ligand and the capture reagent are each an antigen that specifically binds to the antibody.

[14] The method according to any of [1] to [13], wherein the solid-phase support is selected from the group consisting of nitrocellulose, cellulose acetate, nylon, polyethersulfone, polyvinyl alcohol, polyester, glass fiber, polyolefin, cellulose, and artificial polymers composed of mixtures of the above fibers.

[15] A kit for detecting an analyte in a specimen comprising a detection apparatus comprising a solid-phase support onto which a capture reagent that specifically binds to an analyte in a specimen has been immobilized and a device for supplying a specimen comprising a labeled reagent comprising a ligand that specifically binds to the analyte.

[16] The kit according to [15], which further comprises a means of filtering the mixture of the specimen and the labeled reagent that had been brought into contact with each other in the device for supplying a specimen comprising a labeled reagent comprising a ligand that specifically binds to the analyte.

[17] The kit according to [16], wherein the device for supplying a specimen comprises a means of filtration.

[18] The kit according to [17], wherein the means of filtration comprises a labeled reagent.

[19] The kit according to any of [15] to [18], which is a flow-through assay kit.

[20] The kit according to any of [15] to [18], which is an immunochromatography assay kit.

[21] The kit according to any of [15] to [20], wherein the labeled reagent is labeled with a substance selected from the group consisting of an insoluble particulate substance, an enzyme, a fluorescent dye, and a radioisotope.

[22] The kit according to [21], wherein the labeled reagent is an enzyme, and the kit comprises a means of supplying a substrate for the enzyme.

[23] The kit according to any of [15] to [22], wherein the analyte is an antigen, and the ligand and the capture reagent are each an antibody that specifically binds to the antigen.

[24] The kit according to any of [15] to [22], wherein the analyte is an antibody and the ligand and the capture reagent are each an antigen that specifically binds to the antibody.

[25] The kit according to any of [15] to [24], wherein the solid-phase support is selected from the group consisting of nitrocellulose, cellulose acetate, nylon, polyethersulfone, polyvinyl alcohol, polyester, glass fiber, polyolefin, cellulose, and artificial polymers composed of mixtures of the above fibers.

[26] A flow-through assay apparatus for detecting an analyte comprising a solid-phase support onto which a capture reagent that specifically binds to the analyte has been immobilized and a porous material impregnated with a labeled reagent containing a ligand that specifically binds to the analyte, wherein the porous material is contained in an adaptor provided in an upper layer of the solid-phase support.

[27] The apparatus for detecting an analyte according to [26], wherein the labeled reagent is labeled with a substance selected from the group consisting of an insoluble particulate substance, an enzyme, a fluorescent dye, and a radioisotope.

[28] The apparatus for detecting an analyte according to [26] or [27], wherein the analyte is an antigen, and the ligand and the capture reagent are each an antibody that specifically binds to the antigen.

[29] The apparatus for detecting an analyte according to [26] or [27], wherein the analyte is an antibody, and the ligand and the capture reagent are each an antigen that specifically binds to the antibody.

[30] The apparatus for detecting an analyte according to any of [26] to [29], wherein the solid-phase support is selected from the group consisting of nitrocellulose, cellulose acetate, nylon, polyethersulfone, polyvinyl alcohol, polyester, glass fiber, polyolefin, cellulose, and artificial polymers composed of mixtures of the above fibers.

[31] A device for supplying a specimen used for detecting an analyte in a specimen, which comprises a container for accommodating a specimen and a nozzle section for supplying the specimen to an apparatus for detecting an analyte in the specimen, wherein the nozzle section comprises a means of filtering a specimen and a labeled reagent capable of forming a complex with an analyte in an specimen.

[32] The device for supplying a specimen according to [31], wherein the labeled reagent is labeled with a substance selected from the group consisting of an insoluble particulate substance, an enzyme, a fluorescent dye, and a radioisotope.

[33] The device for supplying a specimen according to [31] or [32], wherein the means for filtering a specimen is a filter.

This description includes part or all of the contents as disclosed in the description and/or drawings of Japanese Patent Application No. 2004-018886, which is a priority document of the present application.

EFFECTS OF THE INVENTION

The present invention provides a method for detecting an analyte in a specimen wherein a complex of a capture reagent immobilized on a solid-phase support, an analyte in a specimen, and a labeled reagent is formed. In such a method, a labeled reagent containing a ligand that specifically binds to the analyte is brought into contact with a specimen in advance. Thus, the amount of time that the analyte and the labeled substance are in contact can be regulated, and the analyte can be detected with high sensitivity. Since detection can be carried out by simply supplying the mixture of the analyte and the labeled substance resulting from the contact to the detection apparatus, the analyte can be promptly detected. Further, the mixture of the analyte and the labeled substance may be supplied and subjected to filtration simultaneously, in order to remove impurities from the specimens.

According to the method of the present invention, a step of bringing a specimen into contact with a labeled reagent containing a ligand that specifically binds to the analyte, a step of filtration for removing impurities, and a step of supplying the mixture of the analyte and the labeled reagent to a solid-phase support onto which a capture reagent that specifically binds to the analyte has been immobilized can be carried out in a single step. This enables prompt and sensitive analyte detection.

The method of the present invention involves the use of a device for supplying a specimen that comprises a labeled reagent and a means of filtration. Such use of the device facilitates the performance of a step of bringing a specimen into contact with a labeled reagent containing a ligand that specifically binds to the analyte, a step of filtration for removing impurities, and a step of supplying the mixture of the analyte and the labeled reagent to a solid-phase support onto which a capture reagent that specifically binds to the analyte has been immobilized in a single step. Also, the amount of time that the specimen and the analyte remain in contact can be controlled in the device, and detection sensitivity can be regulated.

DESCRIPTION OF REFERENCE NUMERALS

Figure 1:
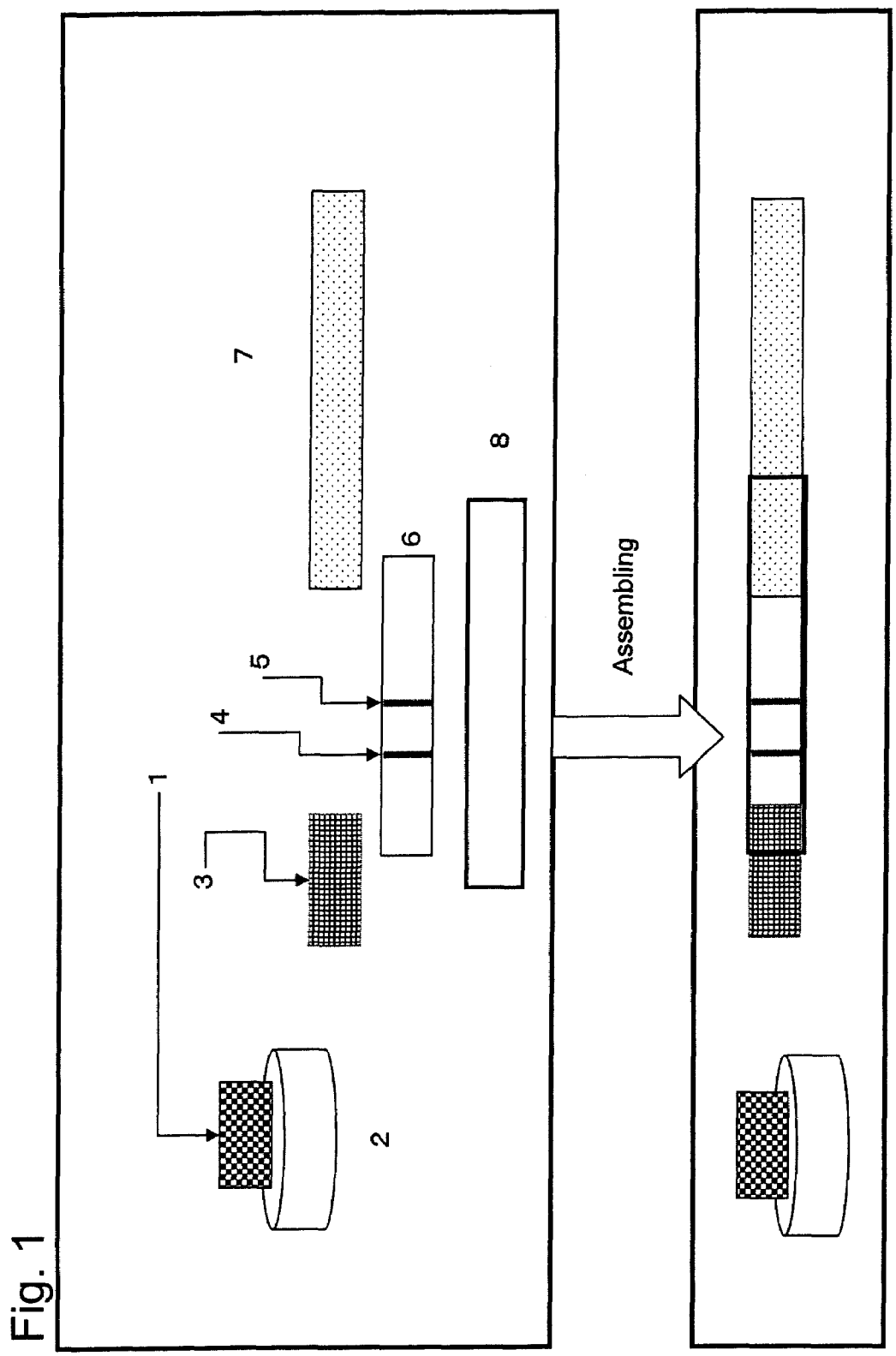
FIG. 1 shows an embodiment of a detection apparatus according to the present invention (labeling substance: an insoluble particulate substance).

1: Labeled reagent
2: Device for supplying a specimen
3: Sample drop site (sample pad)
4: Capture reagent (capture antibody)
5: Control site
6: Solid-phase support (nitrocellulose membrane)
7: Absorption site (absorbent pad)
8: Top laminate or housing
9: Sample application site (sample pad)
10: Dehydration substrate
11: Nozzle
12: Nozzle site
13: Filter
14: Labeled reagent
15: Container for accommodating specimens
16: Space in which a specimen sample and a labeled reagent are temporarily remained and mixed
17: Air vent
18: Housing
19: Solid-phase support
20: Spacer
21: Absorption site
22: Specimen sample
23: Labeled reagent
24: Adaptor
25: Opening
26: Region coated with a capture reagent

PREFERRED EMBODIMENT OF THE INVENTION

Hereafter, the present invention is described in detail.

The present invention provides a method for detecting an analyte in a specimen, and such a method is carried out by, for example, a flow-through assay technique or an immunochromatography assay technique. These techniques involve the use of a membrane-shaped solid-phase support onto which a capture reagent capable of binding to and capturing at least an analyte is immobilized. In the case of the flow-through assay technique, a specimen sample transversely passes across the solid-phase support. In the case of the immunochromatography assay technique, a specimen sample spreads and migrates along the solid-phase support.

In the method of the present invention, a target specimen containing an analyte to be subjected to qualitative and quantitative analysis is prepared so that an analyte is likely to specifically bind to a labeled reagent containing a ligand that specifically binds to the analyte. Such preparation may be carried out chemically with the use of various chemical products such as acids or bases or physically by means of heating, agitation, ultrasonication, or the like. The preparation may be carried out chemically and physically. Specifically, an analyte is often present in a matrix derived from an organism such as a microorganism or cell in the specimen. Thus, the specimen is suspended in an acid solution, a basic solution, a surfactant solution, a denaturation solution, or a buffer, and a microbial or cellular matrix is disrupted via agitation or heating to extract an analyte. Subsequently, the suspension is prepared so as to facilitate specific binding between the analyte and a labeled reagent containing a ligand that specifically binds to the analyte. For example, the pH level is adjusted, the amount of inorganic salts added is adjusted, an additive, such as a surfactant or high-molecular-weight polymer for enhancing specific binding, or a basic compound, is added, or an additive, such as a surfactant or high-molecular-weight polymer for reducing nonspecific reactions, or a basic compound, is added. An example of a solution for preparing the specimen used in the detection apparatus of the present invention is a specimen suspension, the composition of which is disclosed in JP Patent Publication (unexamined) No. 2003-279577A. If the analyte is likely to specifically bind to a labeled reagent containing a ligand that specifically binds to the analyte in the specimen, the specimen may be merely suspended in a solution in which the analyte is likely to undergo specific binding, or the specimen may be used in such a state. If such procedure of preparing a specimen is performed using a device for supplying a specimen, operation is further facilitated.

An analyte to be analyzed by the method of the present invention is not limited. In general, such an analyte is an antigen or antibody. A specimen is not limited, and examples thereof include biological samples, such as whole blood, blood serum, blood plasma, urine, saliva, sputum, sweat, or a nose, throat, nasopharyngeal, or respiratory secretion product, and food extracts, such as meat or vegetable extracts. Typically, a ligand that binds to an analyte is an antibody that specifically binds to an antigen when the analyte is an antigen. When the analyte is an antibody, such a ligand is an antigen that specifically binds to the antibody. In addition, examples of analyte-ligand complex include a receptor-ligand complex and a ligand-receptor complex. The term "labeled reagent" refers to a conjugate of the ligand and an adequate labeling substance. Examples of labeling substances include: metal colloids such as gold colloids; non-metal colloids such as selenium colloids; insoluble particulate substances such as colored resin particles, dye colloids, or colored liposomes; enzymes that catalyze color reactions such as alkaline phosphatase or peroxidase; fluorescent dyes; and radioisotopes.

Subsequently, the specimen sample prepared as described above is brought into contact and mixed with the labeled reagent prior to the supply thereof to the solid-phase support onto which a capture reagent has been immobilized. This results in the formation of a complex of the labeled reagent and the analyte. FIG. 1 schematically shows the method of the present invention, which involves the use of an immunochromatography detection apparatus. When a flow-through detection apparatus is to be used, the immunochromatography detection apparatus shown in FIG. 1 may be exchanged with the flow-through detection apparatus. When a specimen contains an analyte, the specimen can be brought into contact with a labeled reagent to prepare the mixture of the specimen and the labeled reagent. The resulting mixture contains a mixture of the analyte and the labeled reagent, and it further contains a complex of an analyte and a labeled reagent. The sample is prepared in a manner described above so that the analyte is likely to specifically bind to a ligand that specifically binds to the analyte. An excess amount of the labeled reagent is brought into contact with the analyte, and thus, most of the analytes each independently and effectively form a complex selectively with the labeled reagent. A capture reagent is a substance that specifically binds to the analyte. As with the complex of an analyte and a labeled reagent described above, a complex of a capture reagent and an analyte can be, for example, an antigen-antibody, antibody-antigen, receptor-ligand, or ligand-receptor complex. A capture reagent and a labeled reagent may be the same substance. When the analyte has only one site that binds to the aforementioned substance, a complex of a labeled reagent, an analyte, and a capture reagent is not formed. In such a case, a capture reagent and a labeled reagent are required to bind to separate sites of the analyte. A solid-phase support may be composed of any substance as long as the specimen sample can be absorbed and can flow due to the capillary phenomenon. For example, a material constituting the solid-phase support is selected from the group consisting of nitrocellulose, cellulose acetate, nylon, polyethersulfone, polyvinyl alcohol, polyester, glass fiber, polyolefin, cellulose, and artificial polymers composed of mixtures of the above fibers. When the method of the present invention is carried out via a flow-through technique, the solid-phase support may be a membrane of an arbitrary size. A capture reagent is immobilized on the membrane and a region for such a capture reagent is provided on the membrane. When the method of the present invention is carried out via immunochromatography techniques, the support has preferably a shape of strip. The capture reagent may be immobilized on the solid-phase support by conventional techniques, such as adsorption or chemical binding with the utilization of a functional group, such as an amino or carboxyl group.

Subsequently, a mixed sample of a specimen containing a complex of the labeled reagent and the analyte and the labeled reagent are supplied to a solid-phase support onto which a capture reagent that specifically binds to the analyte has been immobilized to form a complex of the labeled reagent, the analyte, and the capture reagent. In the case of flow-through detection, a complex of the labeled reagent and the analyte is captured by a capture reagent when the complex passes through the solid-phase support onto which the capture reagent has been immobilized. Thus, a complex of the labeled reagent, the analyte, and the capture reagent is formed. In the case of immunochromatography detection, the complex is captured by a capture reagent when the complex migrates on the solid-phase support onto which the capture reagent has been immobilized. Thus, a complex of the labeled reagent, the analyte, and the capture reagent is formed. Detection of the presence or absence of the labeled reagent that has been captured by the solid-phase support enables the determination of the presence of the analyte. Since the analyte and the labeled reagent are designed to be brought into contact with each other in advance at a site detached from the solid-phase support, contact between the analyte and the labeled reagent is sufficient to form a complex. Thus, mere action of supplying of a sample to the solid-phase support having a capture reagent immobilized thereon enables simple and prompt formation of a complex of the labeled reagent, the analyte, and the capture reagent. This enables the detection (assay) of an analyte.

The expression "the analyte and the labeled reagent are designed to be brought into contact with each other in advance at a site detached from the solid-phase support" refers to the condition in which a labeled reagent is not included in the solid-phase support, or it is not included at a site where a liquid can be in contact with the solid-phase support by its contact with the solid-phase support, such as a site to which the specimen is supplied, in the case of the immunochromatography apparatus. In such a case, the analyte is brought into contact with the labeled reagent in advance at a site that is not located on the solid-phase support and that is not in contact with the solid-phase support. For example, some conventional immunochromatography detection apparatuses are composed of a solid-phase support in contact with a porous support impregnated with a labeled reagent. In such a conventional apparatus, a porous support impregnated with a labeled reagent also serves as a site to which the specimen is supplied. By the supply of the specimen to such a site, the specimen is brought into contact with a labeled reagent, and the mixture of the specimen and the labeled reagent is immediately transferred to the solid-phase support. Specifically, the specimen is brought into contact with the labeled reagent at a site that is in contact with the solid-phase support in the conventional apparatus. Such contact does not take place at a site detached from the solid-phase support. Unlike the case of such conventional apparatus, such contact is allowed to take place at a site that is not located on the solid-phase support and that is not in contact with the solid-phase support, i.e., at a site detached from the solid-phase support, in order to regulate the amount of time that the specimen and the labeled reagent and the like are in contact in the present invention.

Figure 4A:
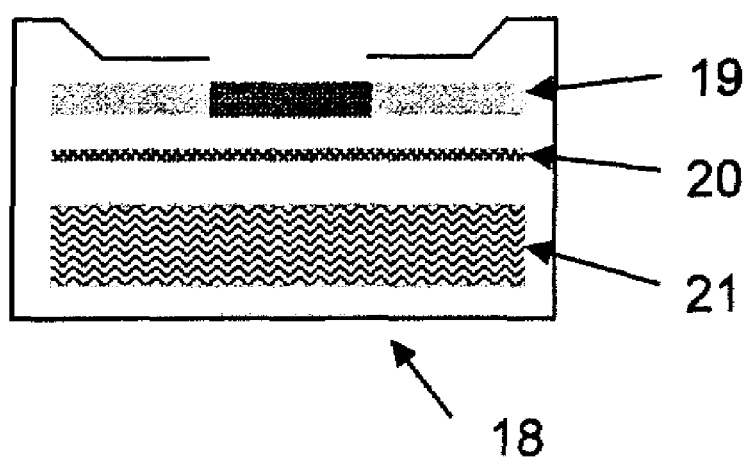
FIG. 4A shows a flow-through detection apparatus according to the present invention, which comprises a housing.
Figure 4B:
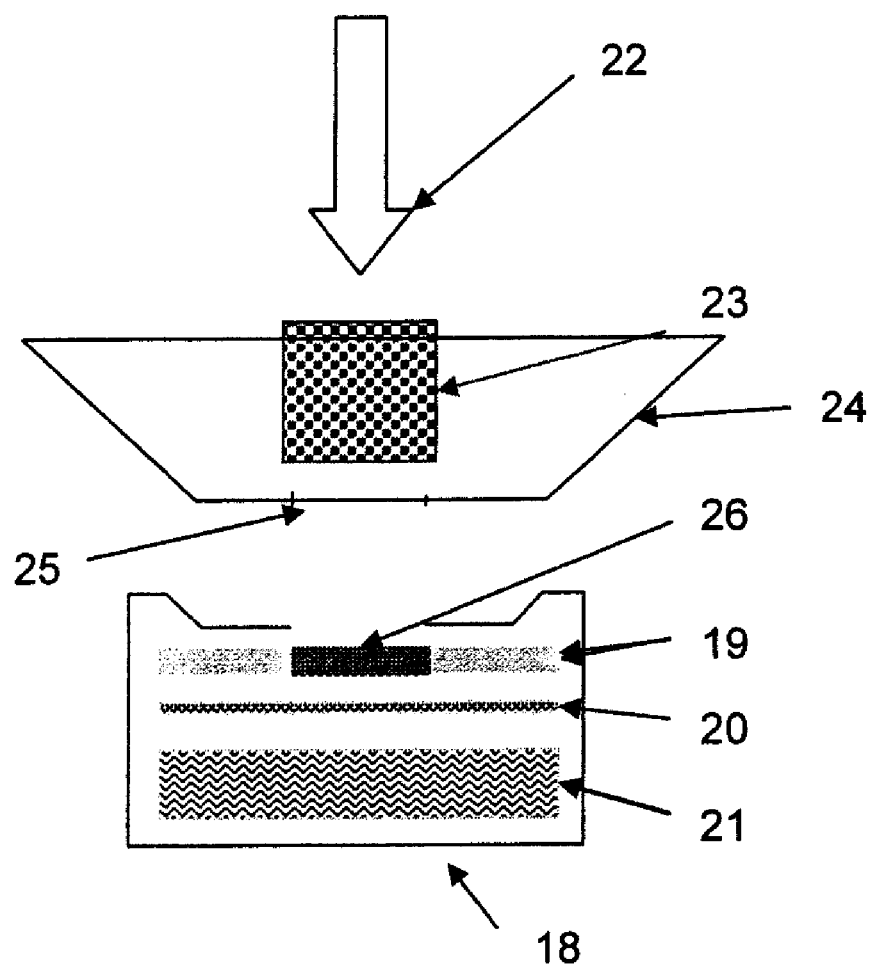
FIG. 4B shows a flow-through detection apparatus according to the present invention, which comprises an adaptor containing a labeled reagent.
Figure 4C:
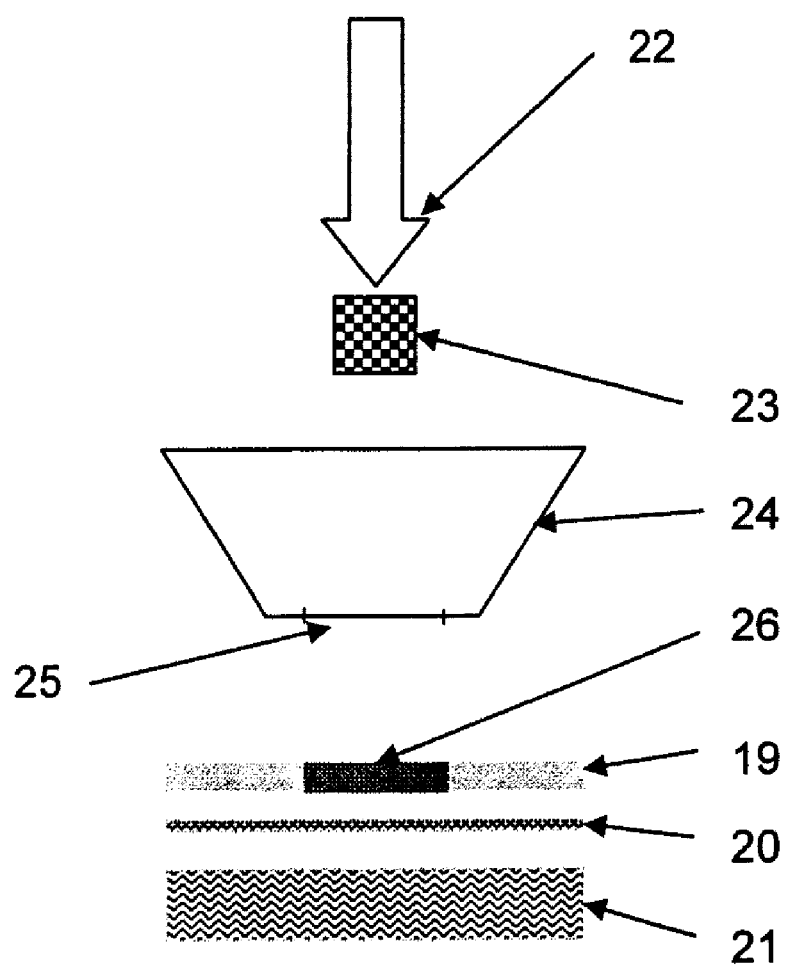
FIG. 4C shows a flow-through detection apparatus according to the present invention, which comprises a labeled reagent incorporated into a device for supplying a specimen.
Figure 4D:
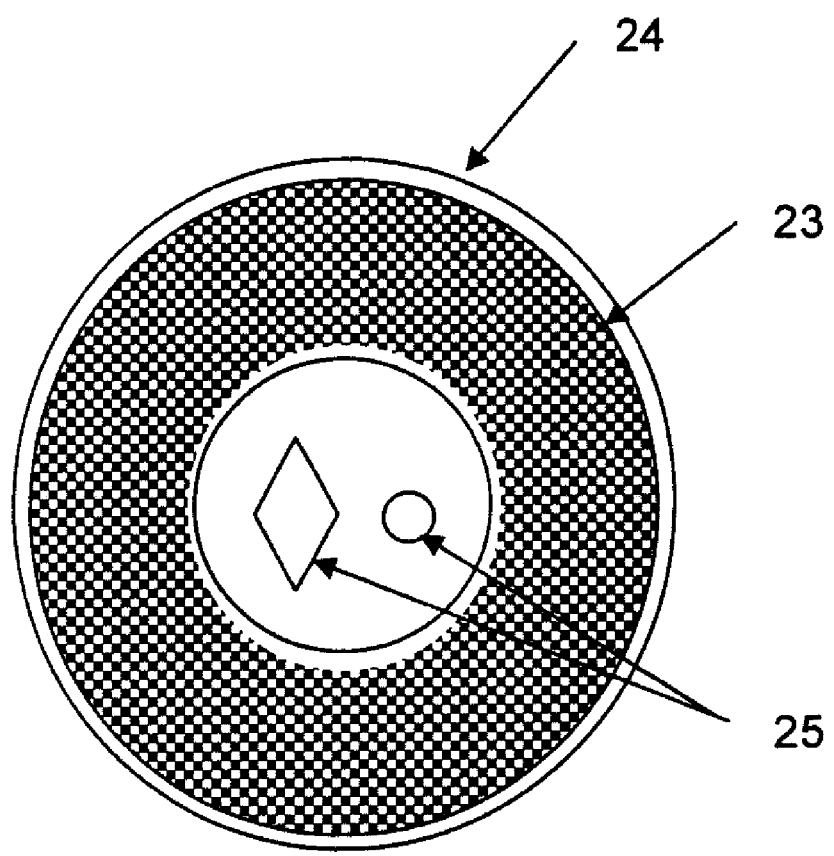
FIG. 4D shows an overhead view of a flow-through detection apparatus according to the present invention, which comprises an adaptor containing a labeled reagent.
Figure 4E:
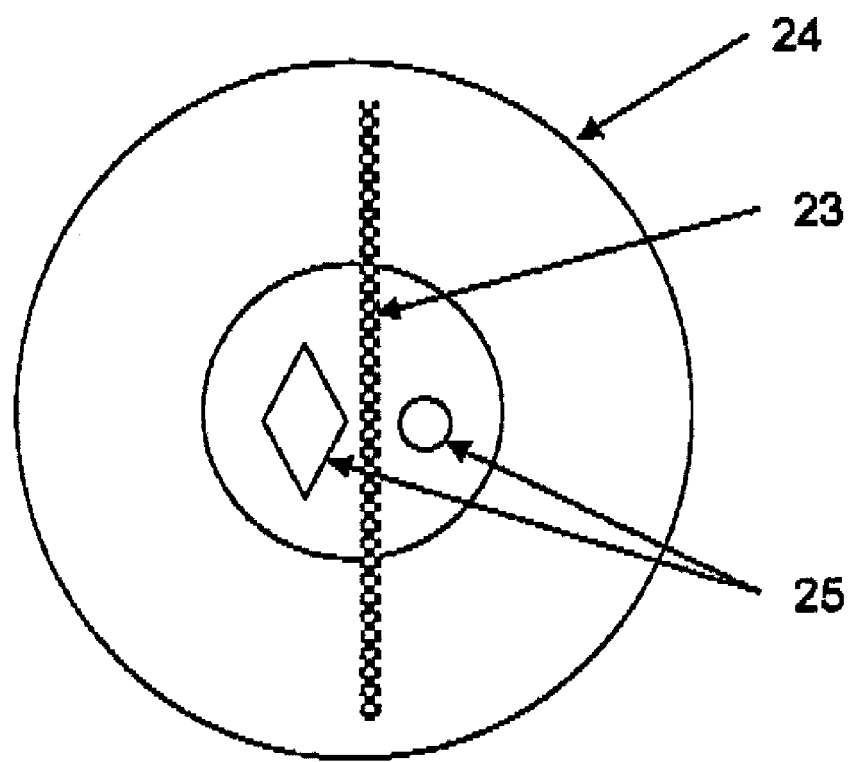
FIG. 4E shows an overhead view of a flow-through detection apparatus according to the present invention, which comprises an adaptor containing a labeled reagent.

In the case of the flow-through detection apparatus, the expression refers to the condition in which the specimen contacts with the labeled reagent in the adapter by adding the specimen into the adapter, where the adapter contains a labeled reagent and is separable from the solid-phase support and is provided in the upper layer of the solid-phase support. Upon introduction of the specimen into the adaptor, the specimen is brought into contact with the labeled reagent in the adaptor. This adaptor is provided with at least one opening for supplying the mixture of the specimen and the labeled reagent to a solid-phase support. After the specimen is brought into contact with the labeled reagent, the mixture of the analyte and the labeled reagent passes through the opening and it is then supplied to the solid-phase support. In fact, the solid-phase support can be in contact with part of the exterior of the adaptor; however, the specimen is brought into contact with the labeled reagent inside the adaptor. It can be accordingly said that such contact takes place at a site detached from the solid-phase support. FIG. 4D and FIG. 4E each show an embodiment of an adaptor containing a labeled reagent. In such embodiment, an opening for transporting the mixture of the analyte and the labeled reagent from the adaptor to the solid-phase support is located at a distance from the porous material impregnated with the labeled reagent. Since the initial contact between the specimen and the labeled reagent takes place at a site where a labeled reagent is present, contact between the specimen and the labeled reagent takes place at a site detached from the solid-phase support.

The labeled reagent may be brought into contact with the specimen in a device for supplying a specimen. The device for supplying a specimen is a component provided outside the detection apparatus, and such a device is a container for accommodating the recovered specimen and performing specific processing thereon. The device comprises a vial, a syringe, a tube, or the like. In addition to a container, the device may comprise a means of filtration for filtering a specimen at the time of supply of the specimen to the detection apparatus. The device for supplying a specimen comprises a container for accommodating a specimen and a section for supplying the specimen contained in the container to the detection apparatus. The section for supplying the specimen comprises a section having a nozzle (a spout) for discharging the specimen from the container, and such a section can also serve as a cover for the container. The section for supplying the specimen is also referred to as a nozzle section or a cover section. When the device for supplying a specimen comprises a means of filtration, the device may be composed of two sections, i.e., a nozzle section composed of a filter housing comprising a filter and a container, as described below. In such a case, the filter housing comprises an opening for allowing the specimen to pass through the filter and an opening for discharging the filtered specimen, and a filter is provided between these openings. The container may be a syringe that allows the specimen to pass through the filter with pressurization, for example.

The labeled reagent may be built into the device for supplying a specimen. The term "built-in" used herein refers to a procedure for allowing the labeled reagent to be comprised in any part of the device and for bringing the specimen into contact with the labeled reagent during the time period between the introduction of the specimen into the device and the supply of the specimen to the detection apparatus. Upon supply of the analyte in the specimen to the site into which the labeled reagent is to be built, the analyte is brought into contact with the labeled reagent. By simply supplying the sample to the capture reagent, accordingly, a complex of the labeled reagent, the analyte, and the capture reagent can be simply and promptly formed. For example, a necessary amount of a labeled reagent may be introduced into a container for collecting a specimen, such as a vial, syringe, or tube, and a necessary amount of a specimen may be added to the container to mix them together. The labeled reagent may be a liquid or lyophilized reagent. Also, the reagent may be adsorbed by an adequate porous material such as glass fiber unwoven fabric, the porous material may be dehydrated and cut into sections (i.e., labeled reagent pads), and such sections may be introduced in the container. In such a case, the liquid specimen is brought into contact with the sections, and the labeled reagent contained in the sections is dissolved in the specimen. In order to render the detection apparatus capable of enduring long-term storage, the reagent is preferably supplied in dry form rather than in liquid form. In order to prepare a dried labeled reagent by lyophilization, batch production is adopted, therefore special large-scale equipment is required.

In contrast, hot air drying enables continuous production by spraying the reagent onto roll paper (i.e., a roll-like support) and drying the sprayed support with the use of a dryer-type hot air blower. The form of the labeled reagent can be adequately selected in accordance with the intended use. In this case, it is preferable that a specimen or a mixture of a specimen and a labeled reagent be filtered in order to remove impurities from the specimen. Filtration may be carried out when supplying a complex of a labeled reagent and an analyte to a detection apparatus. A means of filtration such as a filter may be included in a nozzle section of the device for supplying a specimen, and a mixture of a specimen and a labeled reagent may be supplied through such a filter. In such a case, a labeled reagent may be built into the filter. For example, the filter may absorb the labeled reagent, followed by dehydration. The filter may be brought into contact with a section of the porous material that had absorbed the labeled reagent, followed by dehydration. Alternatively, the filter and the porous material impregnated with a labeled reagent may be built into the filter housing. In this case, the filter may or may not be in contact with the porous material impregnated with a labeling agent. Any filter can be used without particular limitation as long as it can remove impurities such as aggregates or solid matter from the specimen. Examples of filters that can be used include a paper filter, a glass filter, and a membrane filter with a pore diameter of 2 μm or smaller (e.g., 0.22 μm or 0.45 μm). When whole blood is employed as a specimen sample, a filter may have a function of removing erythrocytes. For example, a filter may comprise anti-erythrocyte antibodies to remove erythrocytes. When whole blood is employed, a specimen is brought into contact with a labeled reagent preferably after the removal of erythrocytes with the filter. Examples of a device for supplying a specimen include a container comprising a porous material (a conjugate pad) impregnated with a labeled reagent shown in FIG. 1 and a container comprising a means of filtration shown in FIG. 3. A flow-through detection apparatus includes an adaptor comprising a porous material (a conjugate pad) impregnated with a labeled reagent shown in FIG. 4B.

FIG. 3 shows an embodiment of a device for supplying a specimen comprising a means of filtration and a labeled reagent. The device for supplying a specimen according to the present invention is not limited to those shown in FIG. 1 or FIG. 3. A device of any shape can be used as long as it can hold a specimen and supply the specimen to a sample application site in the detection apparatus. In the device for supplying a specimen shown in FIG. 3, a lower part is a container for holding a specimen, an upper part is a cover section (a nozzle section) of the container having a nozzle for supplying a specimen, and a filter can be provided in the cover section. In FIG. 3A, a filter as a means of filtration is located separately from a porous material impregnated with a labeled reagent, and the porous material impregnated with a labeled reagent is located upstream of the barrier filter. In such a case, the porous material impregnated with a labeled reagent may or may not be immobilized inside the device, such as inside the container, with the use of any suitable means of immobilization. The term "upstream" used herein refers to the upstream area of the flow of the liquid specimen held in a device for supplying a specimen when the specimen is supplied with the use of the device. Besides, a site farther from the nozzle for supplying a specimen in the device is referred to as "upstream," and a site closer to the nozzle is referred to as "downstream." When the device shown in FIG. 3A is used, a specimen is put into the device, and the specimen and the labeled reagent are subjected to upside-down mixing in contact with each other. Thereafter, the mixture may be allowed to pass through the filter so that the mixture would be supplied to the detection apparatus through the nozzle section of the device.

Figure 3A:
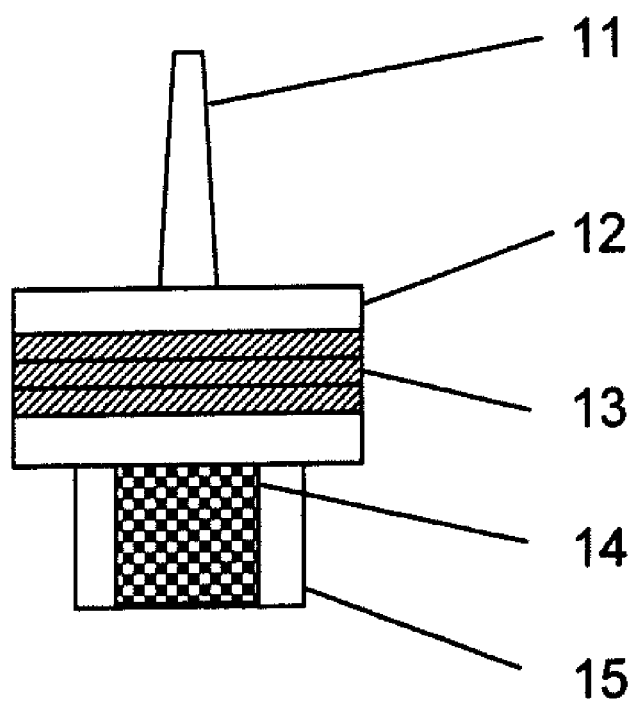
FIG. 3A shows a device for supplying a specimen comprising a means of filtration and a labeled reagent according to the present invention.
Figure 3B:
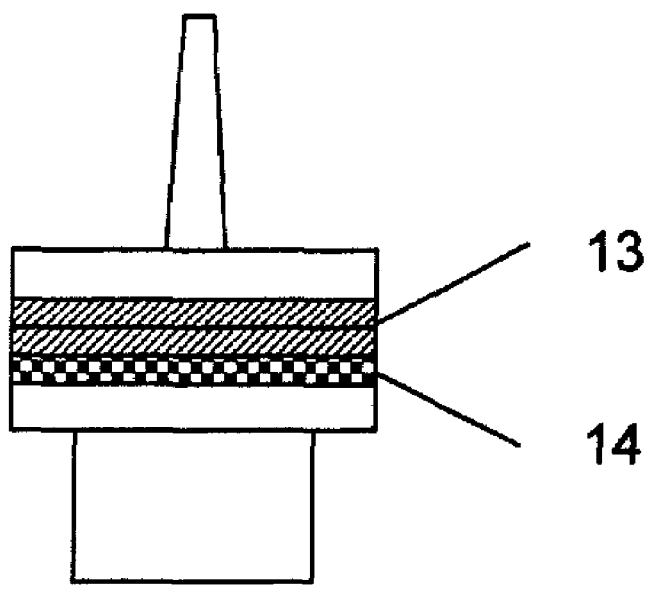
FIG. 3B shows a device for supplying a specimen comprising a means of filtration and a labeled reagent according to the present invention.

FIG. 3B shows a device composed of an integrated combination of a barrier filter in contact with a porous material impregnated with a labeled reagent, and such a porous material is provided on the upstream side of the filter. The porous material impregnated with a labeled reagent can be built into this device as a layer of a barrier filter composed of a single or a plurality of filter layers. In the device shown in FIG. 3B, when a specimen is supplied to a detection apparatus, the specimen passes through the porous material impregnated with a labeled reagent, upon which the labeled reagent is dissolved in the specimen, and the specimen is then brought into contact and mixed with the labeled reagent. The resulting mixture passes through the filter and it is supplied to the detection apparatus through a nozzle section. In the case of the device shown in FIG. 3B, supply of a large volume of a sample solution may be required in order to thoroughly elute the labeled reagent from the porous material. Lack of suitable sample volume may result in an irregular amount of the labeled reagent (i.e., steady performance may not be realized). Also, if a detection apparatus absorbs the solution too rapidly, the detection sensitivity may not be sufficient. Accordingly, it is preferable that the width of the path in the detection apparatus in which liquid flows (the size of the fluid channel) be reduced, for example, by selecting a detection apparatus' membrane having a small pore diameter or by using an adequate adaptor to prolong the amount of time that the specimen is in contact with the labeled reagent and with the capture reagent.

Figure 3C:
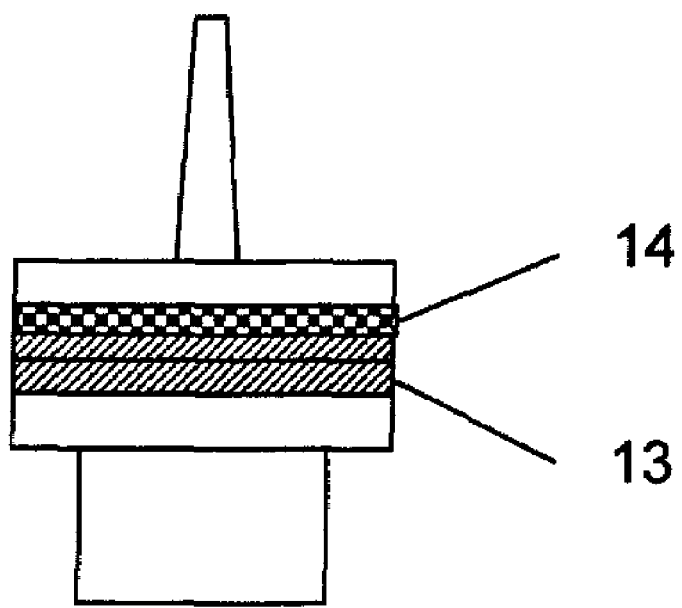
FIG. 3C shows a device for supplying a specimen comprising a means of filtration and a labeled reagent according to the present invention.

FIG. 3C shows a device composed of an integrated combination of a filter in contact with a porous material impregnated with a labeled reagent, and such a porous material is provided on the downstream side of the filter. In the device shown in FIG. 3C, when a specimen is supplied to a detection apparatus, the specimen passes through the filter and then through the porous material impregnated with a labeled reagent, upon which the labeled reagent is eluted in the specimen, and the specimen is brought into contact and mixed with the labeled reagent. The resulting mixture passes through the filter and it is supplied to the detection apparatus through a nozzle section. In the case of the device shown in FIG. 3C, it is preferable that the width of the path in which liquid flows (the size of the fluid channel) be reduced by selecting a detection apparatus' membrane having a small pore diameter or by using an adequate adaptor to prolong the amount of time that the specimen is in contact with the labeled reagent, for the same reason as in the case of the device shown in FIG. 3B.

Figure 3D:
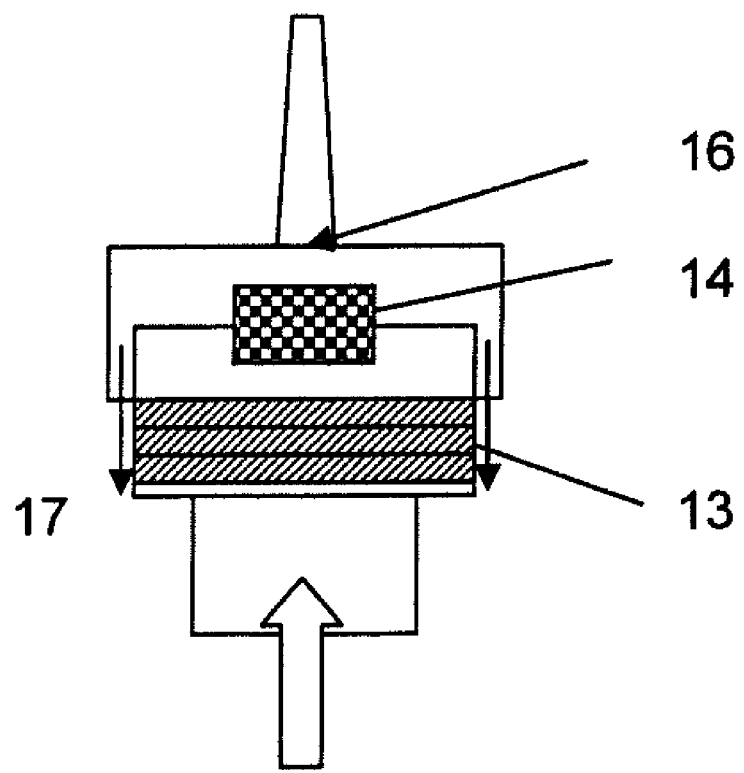
FIG. 3D shows a device for supplying a specimen comprising a means of filtration and a labeled reagent according to the present invention.
Figure 3E:
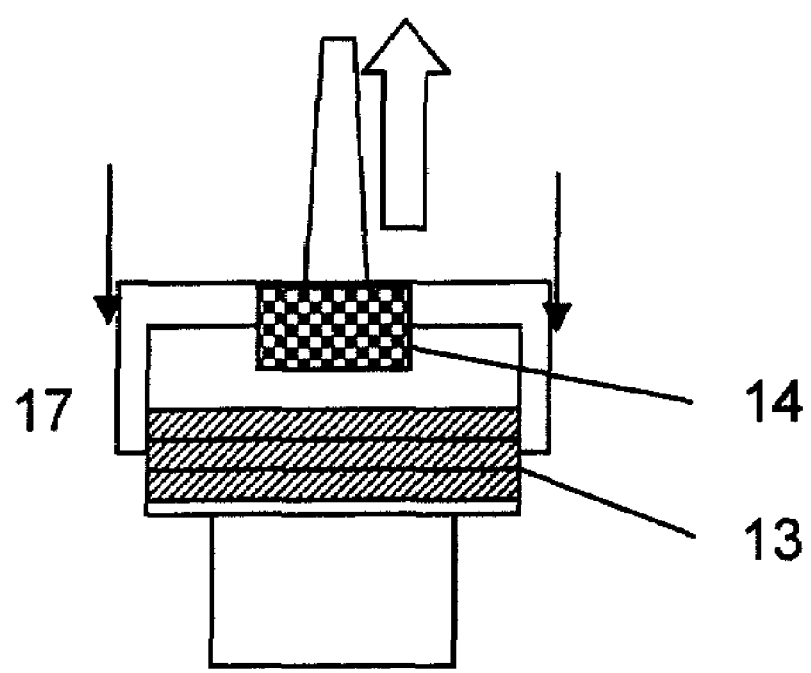
FIG. 3E shows a device for supplying a specimen comprising a means of filtration and a labeled reagent according to the present invention.

FIG. 3D shows a device composed of a filter as a means of filtration separately from a porous material impregnated with a labeled reagent, and such a porous material is provided downstream of the filter. In the device shown in FIG. 3D, an adequate space may be provided between the filter and the nozzle so as to incorporate the porous material impregnated with a labeled reagent into such a space. When a specimen is supplied to a detection apparatus, the specimen passes through the filter, and the specimen is then brought into contact and mixed with the labeled reagent in a space where a porous material impregnated with a labeled reagent is present. Since the specimen is temporarily remained in such a space, the amount of time that the specimen is in contact with the porous material impregnated with the labeled reagent can be prolonged, which results in thorough contact between the specimen and the labeled reagent. In such a case, air vents are preferably provided so as to allow the space to communicate with the exterior of the device. To this end, a nozzle section may be provided separately from a section into which a filter is built, as shown in FIG. 3D. When a mixture of a specimen and a labeled reagent is supplied to a detection apparatus, a nozzle section may be pressed against the section into which the filter is built, in order to block air vents. The specimen is simultaneously supplied dropwise through the nozzle. Thus, built-in of a labeled reagent into a means of filtration enables substantially simultaneous performance of contact mixing of an analyte in a specimen and a labeled reagent and filtration in a single step. Also, built-in of a means of filtration impregnated with a labeled reagent into the device for supplying a specimen enables substantially simultaneous performance of contact mixing of an analyte in a specimen and a labeled reagent, filtration of impurities, and supply of the mixture of the specimen and the labeled reagent to the detection apparatus in a single step. The phrase " . . . enables . . . in a single step" refers to the condition where contact mixing of an analyte in a specimen and a labeled reagent and filtration, or contact mixing of an analyte in a specimen and a labeled reagent, filtration of impurities, and supply of a mixture of a specimen and a labeled reagent to the detection apparatus can be continuously carried out by the single process of supplying a specimen. Thus, the above processes are not necessarily performed simultaneously. The labeled reagent is required to be built-in so as not to be removed before use.

As described above, the device for supplying a specimen according to the present invention can be designed to be capable of regulating the amount of time that a labeled reagent and an analyte in a specimen are in contact and regulating the concentration of a complex of an analyte and a labeled reagent in the mixture of a specimen and a labeled reagent to be supplied to the detection apparatus. In the method shown in FIG. 1 or FIG. 3A, for example, regulation of the amount of time that a specimen and a labeled reagent in a container are in contact is sufficient. In the method involving the use of the device for supplying a specimen as shown in FIG. 4C or FIG. 3B to FIG. 3E, regulation of the flow rate of the specimen when supplying the specimen to the detection apparatus is sufficient. In the case of the flow-through detection method involving the use of an adaptor comprising a labeled reagent as shown in FIG. 4B, the time required for the specimen to migrate from the adaptor to the detection apparatus may be regulated. To this end, the size of the opening through which the specimen migrates from the adaptor to a solid-phase support may be varied or an adequate filter may be provided at the opening, for example. This device has a function of concentrating a complex of an analyte and a labeled reagent. Such function enables performance of an assay having excellent sensitivity and specificity even if the amount of the analyte is small.

A filter may be provided at a site to which the specimen is to be supplied, which is in contact with the solid-phase support of the detection apparatus.

In the case of a flow-through detection apparatus, a porous material impregnated with a reagent, which contains a ligand that specifically binds to the analyte, may be provided in the upper layer of a solid-phase support onto which a capture reagent is immobilized. In such a case, such a porous material is preferably provided so as to avoid contact thereof with the solid-phase support onto which a capture reagent is immobilized. FIG. 4 shows an embodiment of a flow-through detection apparatus of the present invention. The flow-through detection apparatus comprises a laminate of a solid-phase support onto which a capture reagent is immobilized, an absorption site (an absorbent), a spacer, and the like. Such a multilayer construct is accommodated in adequate housing. FIG. 4A shows a flow-through detection apparatus with housing. The porous material impregnated with a labeled reagent may be built into a container-like adaptor, which can be bound to the housing. By supplying a specimen to the adaptor, the porous material impregnated with a labeled reagent is brought into contact and mixed with the specimen in the adaptor, an analyte in a specimen forms a complex with a labeled reagent, such a complex is allowed to migrate to a support onto which a capture reagent located downstream of the opening provided at the bottom of the adaptor is immobilized, and the complex is captured by an immobilized capture reagent to form a complex. When a complex is formed, it is recognized as an aggregated labeled reagent. In this case, an adaptor may or may not be in contact with a support onto which a capture reagent is immobilized. In the apparatus shown in FIG. 4A, housing is provided separately from a solid-phase support or the like. In order to fix a solid-phase support in housing, the housing may be brought into contact with the solid-phase support or the like. FIG. 4D and FIG. 4E each show an overhead view of an embodiment of an adaptor. The shape of the adaptor is not limited to the shapes shown in such figures. The adaptor shown in such figures comprises rhombic and round openings. In the apparatus involving such an adaptor, a ligand that specifically binds to an analyte or a control reagent may be immobilized on a solid-phase support so as to conform to the size and the shape of the opening of the adaptor. The devices shown in FIG. 4D and in FIG. 4E have rhombic and round openings, and ligands and control reagents are immobilized on solid-phase supports corresponding to the openings.

When the adaptor comprises a labeled reagent, the labeled reagent should be supplied in a manner such that it would not block the region at which a specimen is supplied to the detection apparatus; i.e., the opening of the adaptor should not be blocked. In FIG. 4D, a labeled reagent is present around the opening. In FIG. 4E, a labeled reagent is present between two openings. The devices shown in such figures are just examples. It is important that the labeled reagent is built-in so as not to interfere with the supply of the mixture of the analyte and the labeled reagent to the solid-phase support. In the case of FIG. 4D and FIG. 4E, specifically, the porous material impregnated with a labeled reagent may be immobilized at a site shown in FIG. 4D or 4E via a suitable means of immobilization. The means of immobilization is not particularly limited. For example, the inner surface of the lower part of the adaptor may be provided with a concavity, which is capable of holding the porous material. Alternatively, the porous material may be attached to the inside of the adaptor with the aid of an adhesive, which would not affect the detection. Thus, aggregated images can be observed without removing an adaptor.

Figure 2:
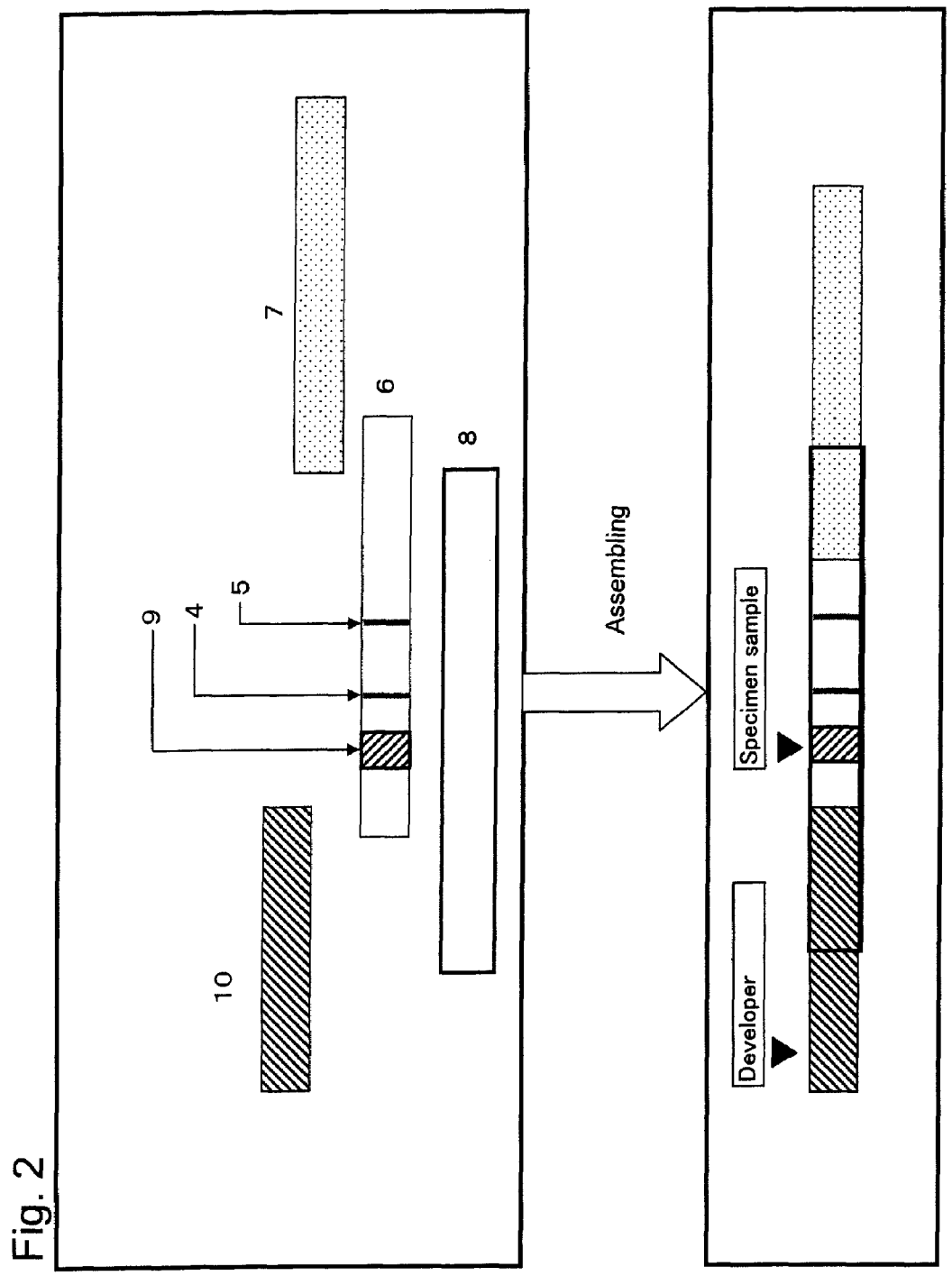
FIG. 2 shows an embodiment of a detection apparatus according to the present invention (labeling substance: an enzyme).

When an enzyme is employed as a labeled reagent, a complex of a labeled reagent and an analyte is first supplied, and an enzyme substrate may be then supplied to the solid-phase support. The substrate may be supplied by dropping a substrate solution to the device or alternatively, a substrate supply means having substrate may be previously provided in the device. In the latter case, for example, a porous material, such as glass fiber or an unwoven fabric of polystyrene that had absorbed a substrate solution and had been dehydrated, may be provided upstream of the site to which a sample is to be supplied of an immunochromatography detection apparatus, and after supplying a sample to the site, an adequate developer solution, such as water or a buffer may then be supplied dropwise to the site into which the substrate has been built. Through such procedures, the substrate is spread, it reaches the site at which a complex of a labeled reagent, an analyte, and a capture reagent is formed, and color is developed with the function of an enzyme as a labeled reagent. FIG. 2 schematically shows a method of detection involving the use of the immunochromatography detection apparatus, when an enzyme is used as a labeled reagent. In the case of a flow-through detection apparatus, for example, a porous material or polystyrene unwoven fabric, such as a glass fiber that had absorbed a substrate solution and was dehydrated, is separately prepared, a mixture of an analyte and a labeled reagent is supplied to the detection apparatus, the adaptor comprising a porous material impregnated with a substrate solution is mounted on the detection apparatus, and a solution for spreading the substrate solution may be supplied. In such a case, the adaptor shown in FIG. 4 may be exchanged.

The detection apparatus of the present invention may be held in the housing as in the case of the flow-through detection apparatus. Such housing can prevent, for example, deterioration due to ultraviolet rays or moisture in the air. For example, a resin case of a suitable size may be employed as housing, and the apparatus of the present invention may be held inside the case. The surface of the solid-phase support onto which a capture reagent is immobilized may be covered with a resin film or the like (a top laminate).

A component capable of regulating the reaction time between the mixture of the analyte and the labeled reagent, and the capture reagent may also be added. The duration of the reaction among the mixture of the analyte, labeled reagent and the capture reagent can be regulated in the following manner. In the case of a flow-through detection apparatus, the time required for the mixture to transversely pass through the solid-phase support onto which the capture reagent is immobilized, i.e., the amount of time that the mixture and the capture reagent are in contact, may be regulated. In the case of an immunochromatography detection apparatus, the time required for the mixture to become spread and migrate along the solid-phase support onto which the capture reagent is immobilized, i.e., the amount of time that the mixture and the capture reagent are in contact, may be regulated. Such contact time can be regulated by controlling the flow rate of liquid containing the mixture of the analyte and the labeled substance. Provision of a component that can slow down the flow rate in part of the flow-through detection apparatus or immunochromatography detection apparatus can prolong the amount of time that the mixture of the analyte and the labeled substance, and the capture reagent are in contact, which enables more sensitive detection. For example, a layer or site composed of a porous material with a small pore diameter may be provided upstream of the solid-phase support. Provision of a component that can gain the flow rate in part of the flow-through detection apparatus or immunochromatography detection apparatus can shorten the amount of time that the mixture and the capture reagent are in contact, which enables more prompt detection. For example, an absorption site at which liquid is absorbed may be provided downstream of the solid-phase support. Provision of such components can automatically minimize the reaction time. Thus, an assay that is excellent in convenience, sensitivity, and specificity can be performed.

The detection apparatus used in the method according to the present invention may further comprise a control reagent. Furthermore, the apparatus may comprise a sample application site or a specimen absorption site. A control reagent is not particularly limited. For example, a substance to which a ligand in the labeled reagent binds can be used. A control reagent may be immobilized on a membrane at a site different from the site onto which a capture reagent is immobilized in the flow-through detection method. In the case of the immunochromatography detection method, a control reagent may be immobilized downstream of the site onto which a capture reagent is immobilized. The sample application site absorbs a mixture of a specimen and a labeled reagent and supplies the absorbed mixture to the solid-phase support onto which a capture reagent is immobilized. The sample application site is preferably composed of a porous material that is capable of absorbing a given amount of liquid. For example, glass fiber or polystyrene unwoven fabric made may be employed. The absorption site is capable of absorbing liquid, i.e., it absorbs a specimen that has passed through a capture section to regulate the flow of the specimen. In the flow-through detection method, for example, an absorption site may be provided underneath the membrane onto which a capture reagent is immobilized. In the immunochromatography detection method, an absorption site may be provided at the lowermost stream of the detection apparatus. For example, an absorption section made of paper may be employed as an absorbent pad.

EXAMPLES

The present invention is described in greater detail with reference to the following examples, although the technical scope of the present invention is not limited to these examples. With regard to the following examples, conventional methods are employed as comparative examples.

Example 1

Detection of Influenza A Viruses Using a Flow-Through Detection Apparatus (1) Preparation of Colloidal Gold Antibodies Colloidal gold (10 ml) was fractionated, and the pH level was adjusted to 7.0 with the aid of 100 mM potassium carbonate. Anti-influenza A virus monoclonal antibodies were dialyzed with a 2 mM boric acid solution, centrifuged, and purified. A 2 mM boric acid solution was added thereto to prepare a solution containing the antibodies at a concentration of approximately 100 μg/ml. A fraction of the resulting solution containing the anti-influenza A virus monoclonal antibodies at a final concentration of 10 μg/ml was thoroughly agitated and added to the colloidal gold. Five minutes thereafter, 1 ml of 10% BSA was added and the mixture was moderately agitated with a rotator for 10 minutes. The entire amount of the solution was transferred to a centrifugation tube and centrifugation was carried out at 14,000 rpm for 30 minutes at 4° C. After the centrifugation, the supernatant was suctioned, and 1 ml of a solution comprising 10 mM Tris-HCl buffer (final concentration), 1% BSA, and 150 mM sodium chloride was added to the colloidal gold that had been precipitated and the colloidal gold that had been sensitized with the anti-influenza A virus monoclonal antibodies to prepare a suspension.

(2) Dehydration of Colloidal Gold Antibodies

The antibody-sensitized colloidal gold prepared in the section above ($OD_{520}$=8.0) was sprayed on a polystyrene unwoven fabric of 10 mm×300 mm at a flow rate of 10 μl/cm using a positive pressure spray apparatus (Biojet, BioDot Inc.). Subsequently, the antibody-sensitized colloidal gold was dehydrated under reduced pressure in a decompressor for 1 hour to prepare a dehydrated antibody-sensitized colloidal gold pad. The pad was cut at intervals of 7 mm and used.

(3) Immobilization of Antibodies onto Membrane Filter for Diagnosis and Preparation of Detection Apparatus Immobilization of anti-influenza virus monoclonal antibodies (mouse) onto a nitrocellulose filter was explained as an example.

Anti-influenza virus monoclonal antibodies (mouse), which were subjected to affinity purification with a protein A column, were prepared. A buffer containing antibodies suspended therein was substituted with a 0.1% trehalose-containing 10 mM citrate buffer (pH 4.0) using a Sephadex G-25 gel filtration column.

The antibodies were diluted with the 0.1% trehalose-containing 10 mM citrate buffer (pH 4.0) to adjust the absorbance at 280 nm to 1.0, a suitable amount thereof (e.g., 10 μl/apparatus (device) in the case of a flow-through detection (diagnosis) apparatus) was supplied dropwise to a nitrocellulose membrane provided in the detection apparatus, and the resultant was then allowed to stand at 45° C. for 40 minutes, followed by dehydration.

(4) Detection Method (a Conventional Method as a Comparative Example)

A sample that may contain influenza A viruses was suspended in an adequate buffer. The resulting solution (500 μl) and 50 μl of antibody-sensitized colloidal gold ($OD_{520}$=8.0) were mixed and allowed to react with each other. After the reaction was carried out for a given period of time, the total amount of the sample was supplied dropwise to the detection apparatus (device), following filtration through a filter (e.g., 0.22 μm). After the whole liquid was absorbed by the membrane member, if the membrane member is stained with the color of a gold colloid (e.g., red to red-brown) at a region to which the anti-influenza virus monoclonal antibodies have been adsorbed, this indicates that the sample contains influenza A viruses. If the membrane member does not undergo changes in hue, this indicates that the sample does not contain influenza A viruses.

(5) Detection Method 1 (Incorporation of a Detection Reagent on the Device Side)

In advance, the pad prepared in (2) above was held into the adaptor of the detection apparatus (device) so as not to block a test region or a sample-absorbing region and so as not to be removed from the adaptor (FIG. 4B). A sample (500 μl), which was deduced to contain influenza A viruses, was filtered through a sample-barrier filter, and the total amount of the sample was supplied dropwise to the pad. After the whole liquid has been absorbed by the membrane member, if the membrane member is stained with the color of a gold colloid (e.g., red to red-brown) at a region to which the anti-influenza virus monoclonal antibodies have been immobilized, this indicates that the sample contains influenza A viruses. If the membrane member does not undergo changes in hue, this indicates that the sample does not contain influenza A viruses.

(6) Detection Method 2 (Incorporation of a Detection Reagent on the Sample Filter Side)

In advance, the pad prepared in (2) above was built into the sample filter so as not to be removed therefrom (FIG. 3). The resultant was mounted on a vessel containing 500 μl of a sample, which may contain influenza A viruses. The resultant was subjected to upside-down mixing, dehydrated antibody-sensitized colloidal gold and samples were thoroughly mixed in the vessel, and the total amount of the resultant was supplied dropwise to the device. After the whole liquid has been absorbed by the membrane member, if the membrane member is stained with the color of a gold colloid (e.g., red to red-brown) at a region to which the anti-influenza virus monoclonal antibodies have been immobilized, this indicates that the sample contains influenza A viruses. If the membrane member does not undergo changes in hue, this indicates that the sample does not contain influenza A viruses.

Example 2

Detection of Influenza A Viruses Using Immunochromatography (Lateral Flow) Apparatus (1) Preparation of Antibody-Sensitized Colloidal Gold Colloidal gold (10 ml) was taken, and the pH level was adjusted to 7.0 with the addition of 100 mM potassium carbonate. The anti-influenza A virus monoclonal antibodies were dialyzed with a 2 mM boric acid solution, centrifuged, and purified. A 2 mM boric acid solution was added thereto to prepare a solution containing the antibodies at a concentration of 100 μg/ml. A fraction of the resulting solution containing the anti-influenza A virus monoclonal antibodies at a final concentration of 10 μg/ml was thoroughly agitated and added to the colloidal gold. Five minutes thereafter, 1 ml of 10% BSA was added and the mixture was moderately agitated with a rotator for 10 minutes. The entire amount of the solution was transferred to a centrifugation tube and centrifugation was carried out at 14,000 rpm for 30 minutes at 4° C. After the centrifugation, the supernatant was suctioned, and 1 ml of a solution comprising 10 mM Tris-HCl buffer (final concentration), 1% BSA, and 150 mM sodium chloride was added to the colloidal gold that had been precipitated and the colloidal gold that had been sensitized with the anti-influenza A virus monoclonal antibodies to prepare a suspension.

(2) Dehydration of Colloidal Gold Antibodies

The antibody-sensitized colloidal gold prepared in the section above ($OD_{520}$=6.0) was sprayed on a polystyrene unwoven fabric of 10 mm×300 mm at a flow rate of 10 μl/cm using a positive pressure spray apparatus (Biojet, BioDot Inc.). Subsequently, the antibody-sensitized colloidal gold was dehydrated under reduced pressure in a decompressor for 1 hour to prepare a dehydrated antibody-sensitized colloidal gold pad. The pad was cut at intervals of 5 mm and used.

(3) Preparation of Immunochromatography Detection Apparatus

Trace amounts of anti-influenza virus monoclonal antibodies (about 2 μl) were supplied dropwise to the membrane member that detects influenza A viruses, the resultant was allowed to stand for a given period of time (for example, for 10 to 60 minutes), and it was then allowed to adsorb on the membrane member.

(4) Detection Method

A sample that may contain influenza A viruses is suspended in a suitable buffer. The resulting solution (200 μl) and 30 μl of antibody-sensitized colloidal gold ($OD_{520}$=1.0) were mixed and allowed to react with each other. After the reaction was carried out for a given period of time, the total amount of the sample was supplied dropwise to the pad (the sample application site), following filtration through a filter (e.g., 0.22 μm). After the liquid is spread over the membrane member, if the membrane member is stained with the color of a gold colloid (e.g., red to red-brown) at a region to which the anti-influenza virus monoclonal antibodies have been immobilized, this indicates that the sample contains influenza A viruses. If the membrane member does not undergo changes in hue, this indicates that the sample does not contain influenza A viruses.

(5) Detection Method 1 (Incorporation of a Detection Reagent on the Sample Barrier Filter Side)

In advance, the pad prepared in (2) above was built into the sample barrier filter so as not to be removed therefrom (FIG. 3). The resultant was mounted on a container comprising 200 μl of the sample that may contain influenza A viruses. The resultant was subjected to upside-down mixing, the dehydrated antibody-sensitized colloidal gold was thoroughly mixed with the sample in the container, and the entire amount of the mixture was then supplied dropwise to the immunochromatography apparatus. After the liquid is spread over the membrane member, if the membrane member is stained with the color of a gold colloid (e.g., red to red-brown) at a region to which the anti-influenza virus monoclonal antibodies have been immobilized, this indicates that the sample contains influenza A viruses. If the membrane member does not undergo changes in hue, this indicates that the sample does not contain influenza A viruses.

Assay Procedures and Results

TABLE 1

Detection of influenza A virus using a flow-through detection apparatus

|  | Before improvement (comparative example) | After improvement-1 | After improvement-2 |
|---|---|---|---|
| Assay procedures | (i) An antibody-sensitized colloidal gold solution was prepared. (ii) The antibody-sensitized colloidal gold solution was mixed with a sample solution. (iii) A sample filter was mounted. (iv) A sample was supplied dropwise to the device. (v) The device was allowed to stand at room temperature until absorption was completed. (vi) Determination was carried out. | (i) An adaptor (FIG. 4B) comprising a sample filter was mounted. (ii) A sample was supplied dropwise to the device. (The device comprises an antibody-sensitized colloidal gold pad.) (iii) The device was allowed to stand at room temperature until absorption was completed. (vi) Diagnosis was carried out. | (i) A sample filter was mounted. (The filter comprises an antibody-sensitized colloidal gold pad (FIG. 3).) (ii) A sample was supplied dropwise to the device. (iii) The device was allowed to stand at room temperature until absorption was completed. (vi) Determination was carried out. |
| Number of steps | 6 | 4 | 4 |
| Test results | Determination | Determination | Determination |
| Strong positive specimens | +++ | +++ | +++ |
| Weak positive specimens | + | + | + |
| Negative specimens | − | − | − |

TABLE 2

Detection of influenza A virus using an immunochromatography detection apparatus

|  | Before improvement (comparative example) | After improvement |
|---|---|---|
| Assay procedures | (i) An antibody-sensitized colloidal gold solution was prepared. (ii) The antibody-sensitized colloidal gold solution was mixed with a sample solution. (iii) A sample filter was mounted. (iv) A sample was supplied dropwise to the device. (v) The device was allowed to stand at room temperature until absorption was completed. (vi) Determination was carried out. | (i) A sample filter was mounted. (The filter comprises an antibody-sensitized colloidal gold pad (FIG. 3).) (ii) A sample was supplied dropwise to the device. (iii) The device was allowed to stand at room temperature until absorption was completed. (vi) Determination was carried out. |
| Number of steps | 6 | 4 |
| Test results | Determination | Determination |
| Strong positive specimens | +++ | +++ |
| Weak positive specimens | + | + |
| Negative specimens | − | − |

All publications, patents, and patent applications cited herein are incorporated herein by reference in their entirety.

What is claimed is:

1. A flow-through assay apparatus for detecting an analyte, comprising (A) a solid-phase support onto which a capture reagent that specifically binds to the analyte has been immobilized and (B) a porous material impregnated with a labeled reagent containing a ligand that specifically binds to the analyte,
    wherein the porous material is contained in an adaptor that
        (i) is provided in an upper layer of the solid-phase support and (ii) is contacted with the solid-phase support, and
    wherein the porous material is configured such that (iii) the analyte and the labeled reagent are contacted and mixed within the porous material and (iv) the porous material does not cover the opening of the adaptor, whereby aggregated images are observable without removing the adaptor.

2. The apparatus for detecting an analyte according to claim 1, wherein the labeled reagent is labeled with a substance selected from the group consisting of an insoluble particulate substance, an enzyme, a fluorescent dye, and a radioisotope.

3. The apparatus for detecting an analyte according to claim 1, wherein the analyte is an antigen, and the ligand and the capture reagent are each an antibody that specifically binds to the antigen.

4. The apparatus for detecting an analyte according to claim 1, wherein the analyte is an antibody, and the ligand and the capture reagent are each an antigen that specifically binds to the antibody.

5. The apparatus for detecting an analyte according to any one of claims 1 to 4, wherein the solid-phase support is selected from the group consisting of nitrocellulose, cellulose acetate, nylon, polyethersulfone, polyvinyl alcohol, polyester, glass fiber, polyolefin, cellulose, and artificial polymers composed of mixtures of the above fibers.

* * * * *